United States Patent [19]

Insley et al.

[11] Patent Number: 4,755,178
[45] Date of Patent: Jul. 5, 1988

[54] SORBENT SHEET MATERIAL

[75] Inventors: Thomas I. Insley; Daniel E. Meyer, both of Stillwater, Minn.

[73] Assignee: Minnesota Mining and Manufacturing Company, St. Paul, Minn.

[21] Appl. No.: 873,126

[22] Filed: Jun. 11, 1986

Related U.S. Application Data

[63] Continuation of Ser. No. 594,737, Mar. 29, 1984, abandoned.

[51] Int. Cl.⁴ .............................................. A61F 13/16
[52] U.S. Cl. .................................... 604/367; 210/511;
428/221; 428/283; 428/288; 428/903; 428/913;
604/358; 604/366
[58] Field of Search ....................... 604/358, 366, 367;
428/283, 221, 288, 903, 913; 210/511

[56] References Cited

U.S. PATENT DOCUMENTS

| | | | |
|---|---|---|---|
| 3,670,731 | 6/1972 | Harmon | 128/284 |
| 3,971,373 | 7/1976 | Braun | 128/146.2 |
| 3,981,100 | 9/1976 | Weaver et al. | 47/58 |
| 4,011,067 | 3/1977 | Carey, Jr. | 55/354 |
| 4,103,062 | 7/1978 | Aberson et al. | 428/283 |
| 4,105,033 | 8/1978 | Chatterjee et al. | 128/285 |
| 4,118,531 | 10/1978 | Hauser | 428/224 |
| 4,235,237 | 11/1980 | Mesek et al. | 128/284 |
| 4,426,417 | 1/1984 | Meitner et al. | 428/195 |
| 4,429,001 | 1/1984 | Kolpin et al. | 428/283 |

FOREIGN PATENT DOCUMENTS

| | | |
|---|---|---|
| 0080382 | 1/1983 | European Pat. Off. . |
| 2373274 | 7/1978 | France . |
| 2006614 | 10/1979 | United Kingdom . |
| 2061339A | 5/1981 | United Kingdom . |
| 2098871A | 12/1981 | United Kingdom . |
| 2113731A | 8/1983 | United Kingdom . |

OTHER PUBLICATIONS

Wente, Van A., "Superfine Thermoplastic Fibers", in Industrial Engineering Chemistry, vol. 48, pp. 1342 et seq (1956).

Report No. 4364 of the Naval Research Laboratories, published May 25, 1954, entitled "Manufacture of Superfine Organic Fibers" by Wente, Van A., Boone, C.D., and Fluharty, E.L.

Primary Examiner—James J. Bell
Attorney, Agent, or Firm—D. M. Sell; J. A. Smith; C. Truesdale

[57] ABSTRACT

Sorbent sheet products are prepared comprising a coherent fibrous web that includes entangled blown fibers and liquid transport fibers intermingled with the blown fibers and an array of solid high sorbency liquid-sorbent polymeric particles uniformly dispersed and physically held within the web. The particles swell upon sorption of liquid, and the transport fibers cause increased and more rapid sorption of liquid by conducting the liquid from external portions of the web to internal portions of the web.

20 Claims, 1 Drawing Sheet

SORBENT SHEET MATERIAL

This is a continuation of application Ser. No. 594,737 filed Mar. 29, 1984 now abandoned.

BACKGROUND ART

Many prior workers have sought to increase the sorbency of fibrous web products by addition of "super absorbent" particles, e.g., modified starch or other polymeric particles which sorb and retain under pressure large volumes of liquids, especially aqueous liquids. The previous products prepared by such additions all have had significant limitations. For example, one commercial product, which comprises sorbent particles adhered between two sheets of tissue paper, decomposes in use, whereupon the sorbent particles are washed out of the product and into liquid being treated. Another commercial product, comprising a rather stiff open-mesh fabric or cheese cloth to which essentially a single layer of sorbent particles is adhered, sorbs only limited amounts of liquid.

A different product taught in U.S. Pat. No. 4,103,062 is made by dispersing particles in an air-laid cellulosic fiber web and densifying the web with heat and pressure to increase its strength. However, this product sorbs only a limited amount of liquid, because of the nonexpansible nature of the densified web, and because sorbent particles at the edge of the web swell upon initial liquid intake and prevent permeation of additional liquid into internal parts of the web. U.S. Pat. No. 4,105,033 seeks to avoid such edge blockage by distributing the sorbent particles in spaced layers separated by layers of fibers, but such a construction requires added processing steps and is subject to delamination. In other products sorbent particles are simply cascaded into a loose fibrous web (see U.S. Pat. No. 3,670,731), but both U.S. Pat. No. 4,103,062 and U.S. Pat. No. 4,105,033 note that it is difficult to deposit the particles uniformly, and the particles tend to move within the web during subsequent processing, storage, shipment or use of the web and thereby develop nonuniform properties.

U.S. Pat. No. 4,235,237 teaches a different approach in which a fibrous web is sprayed, immersed or otherwise contacted with sorbent material dispersed in a volatile liquid. Vaporization of the volatile liquid leaves a web in which sorbent particles envelop the fibers, principally at fiber intersections. Disadvantages of this approach include the need for multiple steps to prepare the product, limitations on amount of sorbent that can be added to the web, brittleness of the dried webs, and the tendency for sorbent material to be concentrated at the web surface.

Many of these problems have been overcome by the sorbent sheet product described in U.S. Pat. No. 4,429,001. In this product, an array of solid high-absorbency liquid-sorbent polymeric particles are uniformly dispersed within a coherent web of melt blown fibers. However, even greater improvement in the rate of liquid sorption would be desirable, since swelling of a mass of the high sorbency particles upon initial liquid sorption can still limit rapid permeation of additional liquid into internal parts of the web. Further, the coherency of the web of melt blown fibers tends to somewhat limit the swelling of the high-sorbency particles during liquid sorption. Surprisingly, the present invention provides a product having increased rate of sorption and greater liquid sorbency than the product disclosed in U.S. Pat. No. 4,429,001.

SUMMARY OF THE INVENTION

The present invention provides further advantages over the prior art products and provides a new sorbent sheet product with unique capabilities beyond those of any known prior-art product. Briefly, this new sheet product comprises a coherent fibrous web that includes entangled blown fibers, and liquid transport fibers intermingled with the blown fibers and an array of solid high-sorbency liquid-sorbent polymeric particles uniformly dispersed and physically held within the web, the particles swelling upon sorption of liquid and the transport fibers causing increased and more rapid sorption of liquid by conducting the liquid from external portions of the web to internal portions of the web. Additionally, the web may contain other constituents such as binders and wetting agents. The blown fibers may be prepared by extruding liquid fiber-forming material into a high-velocity gaseous stream, where the extruded material is attenuated and drawn into fibers. A stream of fibers is formed, which is collected, e.g., on a screen disposed in the stream, as an entangled coherent mass. According to the invention, sorbent particles and transport fibers may be introduced into the stream of melt blown fibers, e.g., in the manner taught in U.S. Pat. No. 4,118,531, and the mixture of melt blown fibers, transport fibers and particles is collected as an entangled coherent mass in which the sorbent particles and transport fibers are entrapped or otherwise physically held. A particle-filled fibrous web containing transport fibers is formed in essentially one step, and the only further processing required may be simply cutting to size and packaging for use.

A sheet product of the invention is integral and handleable both before and after immersion in liquid, because the collected blown fibers are extensively tangled or snarled and form a strong coherent web, and the sorbent particles and transport fibers are lastingly held and retained within this web.

Large quantities of liquid can be sorbed at a rapid rate, with the amount dependent principally on the sorption capacity of the individual sorbent particles and the rate of sorption greatly enhanced by the transport fibers. Liquid is rapidly sorbed by sorbent particles located in even the inner parts of the sheet product, due to the sorbent particles being held apart by the web structure and the transport fibers conducting the liquid to particles located in the interior portion of the web. The melt blown fibers of the web are preferably wet by the liquid being sorbed, e.g., as a result of use of a fiber-forming material that is wet by the liquid or by addition of a surfactant during the web-forming process, which further assists sorption.

The sorbent particles swell and expand in size during sorption, and although the blown fibers are extensively entangled, the web of fibers expands as the particles expand and the sorbed liquid tends to be retained in the product even when the product is subjected to pressure. The transport fibers also serve to separate the melt blown fibers, especially when in crimped form, producing a less dense web with greater potential for expansion on sorption of liquid. On sorption of liquid, the transport fibers allow the blown fibers to slip and move to a degree that the fibrous web is pushed apart by the swelling sorbent particles while the web integrity is maintained.

The sorbent sheet product of the invention has a variety of uses, particularly where rapid sorption, high liquid retention and soft hand are desired, such as in disposable incontinent devices, diapers, surgical swabs, bed pads, sanitary napkins and filters for separating water from organic liquids.

DETAILED DESCRIPTION

Figure 1:
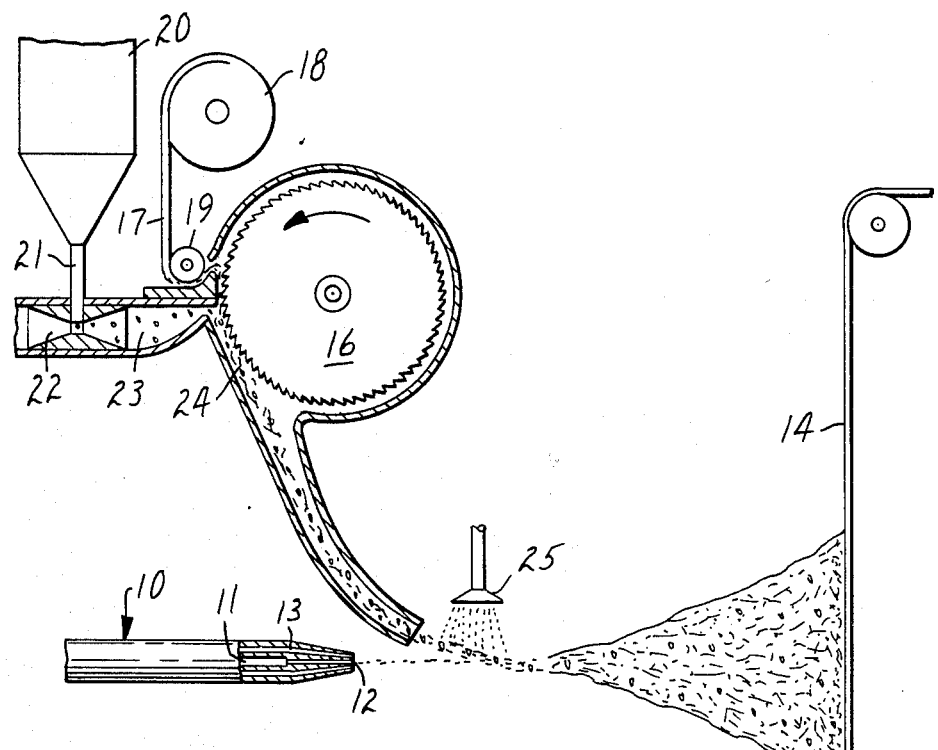
FIG. 1 is a schematic diagram of apparatus used in practicing the present invention.

A representative apparatus useful for preparing sheet product of the invention is shown schematically in FIG. 1. The apparatus is generally similar to that taught in U.S. Pat. No. 4,118,531 for preparing a web of melt-blown fibers and crimped bulking fibers.

This apparatus prepares webs with melt-blown fibers (prepared by extruding molten fiber-forming material and which are preferred in many webs of the invention), but solution-blown and other types of fibers may also be used. The fiber-blowing portion of the illustrated apparatus can be a conventional structure as taught, for example, in Wente, Van A. "Superfine Thermoplastic Fibers", in Industrial Engineering Chemistry, Vol. 48, pages 1342 et seq (1956), or in Report No. 4364 of the Naval Research Laboratories, published May 25, 1954, entitled "Manufacture of Superfine Organic Fibers" by Wente, Van A.; Boone, C. D.; and Fluharty, E. L. Such a structure includes a die 10 which has an extrusion chamber 11 through which liquified fiber-forming material is advanced; die orifices 12 arranged in line across the forward end of the die and through which the fiber-forming material is extruded; and cooperating gas orifices 13 through which a gas, typically heated air, is forced at very high velocity. The high-velocity gaseous stream draws out and attenuates the extruded fiber-forming material, whereupon the fiber-forming material solidifies as fibers during travel to a collector 14. The collector 14 is typically a finely perforated screen, which in this case is in the form of a closed-loop belt, but which can take alternative forms, such as a flat screen or a drum or cylinder. Gas-withdrawal apparatus may be positioned behind the screen to assist in deposition of fibers and removal of gas. Alternatively, two dies may be used and arranged so that the streams of melt blown fibers issuing from them intersect to form one stream that continues to a collector 14.

Figure 2:
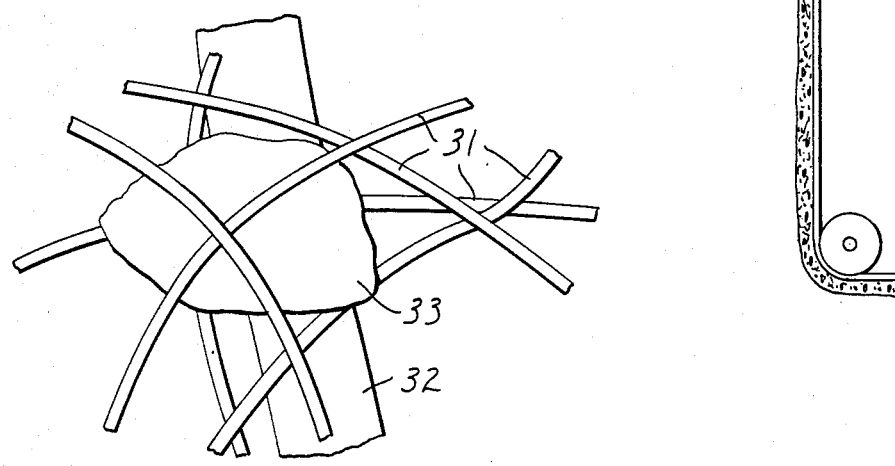
FIG. 2 is a greatly enlarged sectional view of a portion of a sheet product of the invention.

The apparatus shown in FIG. 1 also includes means for introducing sorbent particles and staple transport fibers into the sheet product of the invention. The transport fibers are introduced into the stream of melt blown fibers through the use of a lickerin roll 16. A web 17 of transport fibers, typically a loose, nonwoven web such as prepared on a garnet machine or "Rando-Webber", is supplied from a supply roll 18 under a drive roll 19 where the leading edge engages against the lickerin roll 16. The lickerin roll 16 turns in the direction of the arrow and picks the transport fibers from the leading edge of the web 17, dissociating the transport fibers from one another. The sorbent particles are supplied from a particulate hopper 20 through an inductor 21 which meters the amount of particles flowing into a venturi 22 which is in duct 23. An air stream flows through duct 23 for conveying the sorbent particles. The sorbent particles are conveyed to inclined duct 24 where the fluidized stream of sorbent particles becomes the carrier stream for the transport fibers delivered by the lickerin roll 16. The sorbent particles and transport fibers are conveyed in the air stream through inclined duct 24 and into the stream of melt blown fibers where the sorbent particles and transport fibers become mixed with the melt blown fibers. The mixed stream of melt blown fibers, transport fibers and sorbent particles then continues to the collector 14 where a web of randomly intermixed and intertangled microfibers 31, transport fibers 32, and sorbent particles 33, as shown in FIG. 2, is formed. A spray jet 25 may be used to apply materials, such as binders and wetting agents, to the mixed stream of blown fibers, sorbent particles and transport fibers prior to collection at collector 14.

Melt-blown fibers are greatly preferred for sheet products of the invention, but solution-blown fibers in which the fiber-forming material is made liquid by inclusion of a volatile solvent can also be used. U.S. Pat. No. 4,011,067 describes useful apparatus and procedures for preparing a web of such fibers; however, in preparing sheet products of this invention fiber-forming material is generally extruded through a plurality of adjacent orifices rather than the single orifice shown in the patent.

The sorbent particles and transport fibers are preferably introduced into the fiber stream at a point where the blown fibers have solidified sufficiently that the blown fibers will form only a point contact with the sorbent particles (as taught in U.S. Pat. No. 3,971,373) and transport fibers. However, the sorbent particles and transport fibers can be mixed with the melt blown fibers under conditions that will produce an area contact with the sorbent particles and transport fibers.

Once the sorbent particles and transport fibers have been intercepted in the blown fiber stream, the process for making the sheet product of the invention is generally the same as the process for making other blown fiber webs; and the collectors, methods of collecting, and methods of handling collected webs are generally the same as those for making non-particle-loaded blown fiber webs.

The layer of melt blown fibers, sorbent particles and transport fibers formed in any one revolution of the collection screen, and a completed sheet product of the invention may vary widely in thickness. For most uses of sheet products of the invention, a thickness between about 0.05 and 2 centimeters is used. For some applications, two or more separately formed sheet products of the invention may be assembled as one thicker sheet product. Also, sheet products of the invention may be prepared by depositing the stream of fibers and sorbent particles onto another sheet material such as a porous nonwoven web which is to form part of the eventual sheet product. Other structures, such as impermeable films, can be laminated to a sheet product of the invention through mechanical engagement, heat bonding, or adhesives.

The blown fibers are preferably microfibers, averaging less than about 10 micrometers in diameter, since such fibers offer more points of contact with the particles per unit volume of fiber. Very small fibers, averaging less than 5 or even 1 micrometer in diameter, may be used, especially with sorbent particles of very small size. Solution-blown fibers have the advantage that they may be made in very fine diameters, including less than one micrometer. Larger fibers, e.g., averaging 25 micrometers or more in diameter, may also be prepared, especially by the melt-blowing process.

Blown fibrous webs are characterized by an extreme entanglement of the fibers, which provides coherency and strength to a web and also adapts the web to contain and retain particulate matter and staple fibers. The aspect ratio (ratio of length to diameter) of blown fibers approaches infinity, though the fibers have been reported to be discontinuous. The fibers are long and entangled sufficiently that it is generally impossible to remove one complete fiber from the mass of fibers or to trace one fiber from beginning to end. Despite such entanglement, a sheet product will expand greatly in size during sorption.

The fibers may be formed from a wide variety of fiber-forming materials. Representative polymers for forming melt-blown fibers include polypropylene, polyethylene, polyethylene terephthalate, and polyamides. Representative polymers for forming solution-blown fibers include polymers or copolymers of vinyl acetate, vinyl chloride, and vinylidene chloride. Inorganic materials also form useful fibers. Fibers of different fiber-forming materials may be used in the same sheet product in some embodiments of the invention, either in mixture in one layer or in different layers.

Many of the fiber-forming materials form hydrophobic fibers, which can be undesirable in water sorbing sheet products. To improve the sheet product for such a use, a surfactant in powder or liquid form may be introduced into the sheet product, as by mixing powders with the sorbent particles before they are introduced into the web or spraying liquids onto the web after it is formed. Useful surfactants, which typically comprise molecules having oleophilic and hydrophilic moieties, include dioctyl ester of sodium sulfosuccinate and alkylaryl polyether alcohol. A small amount of the surfactant, such as 0.05 to 1 weight-percent of the sheet product, will generally provide adequate hydrophilicity, but larger amounts can be used. Use of oleophilic fibers together with water-sorbing particles can have the advantage of dual absorption, in that the fibrous web sorbs organic liquids such as oils while the particles sorb water.

As indicated above, the sorbent particles used in the invention are generally super absorbent particles, which rapidly absorb and retain under pressure large quantities of liquids. The preferred particles for sorbing water comprise modified starches, examples of which are described in U.S. Pat. No. 3,981,100, and high-molecular-weight acrylic polymers containing hydrophilic groups. A wide variety of such water-insoluble water-sorbing particles are available commercially, and they typically sorb 20 or more times their weight of water and preferably 100 or more times their weight of water. The amount of water sorbed declines as impurities are included in the water. Alkylstyrene sorbent particles (such as marketed by Dow Chemical Company under the trademark "Imbiber Beads") are useful for sorbing liquids other than water. They tend to sorb 5 to 10 times or more their weight of such liquids. In general, the sorbent particles should sorb at least their own weight of liquid.

The sorbent particles may vary in size, at least from 50 to 3000 micrometers in average diameter. Preferably, the particles are between 75 and 1500 micrometers in average diameter.

The amount of sorbent particles included in a sheet product of the invention will depend on the particular use to be made of the product and will involve balancing the amount of sorbency desired with other properties, such as integrity or strength of the web, or desired web thickness. Generally, sorbent particles account for at least about 20 g/m$^2$ for 100 g/m$^2$ of the blown fiber, more typically 150 to 300 g/m$^2$ for 100 g/m$^2$ of the blown fiber, and can account for as much as 500 g/m$^2$ or more for 100 g/m$^2$ of the blown fiber.

To achieve high loading of sorbent particles, a binding material is preferably added to the product. The binding material should be sufficiently sticky to tack the fibers and particles together, but not bond the web structure itself. The binding material is preferably hydrophilic. The end use of the product may also be considered in selecting the binding material. Materials which may be used as binding material include glycerol, polyethylene glycol, polyols, and polyethers. A small amount of the binding material, such as about 0.5 to 5% by weight of the sheet product, preferably about 0.5 to 2% by weight, is generally sufficient to provide the additional cohesion necessary to retain the sorbent particle within the web when using sorbent particle loadings of 500 weight percent or more based on the weight of the blown fiber.

The transport fibers used in the invention are generally absorbent staple fibers which rapidly absorb and wick the fluid being absorbed. Fibers useful as transport fibers are those having a water retention value of at least about 10%, preferably about 20% and more preferably about 25% when tested according to ASTM Test Method D2402. Fibers having such a water retention value have been found to provide a desired transport of liquid into the interior of the web. Such fibers include rayon, cotton, wool and silk. A particular preferred fiber is "Absorbit" rayon fiber supplied by American Enka Company.

The size of the transport fibers is preferably in the range of about 1 to 50 denier, more preferable about 1 to 30 denier. The size of the transport fibers depends on the end use of the product. Transport fibers of lower denier provide a softer hand and better mechanical hold of the sorbent particles. When using equipment such as a lickerin roll to dissociate the transport fibers during production of the product, the fibers should average between about 2 to 15 centimeters in length. Preferably, the transport fibers are less than about 7 to 10 centimeters in length.

The transport fibers may be crimped to further enhance the anti-blocking effect provided by the fibers. Crimped staple transport fibers provide additional freedom of expansion to the product as the sorbent particles swell during liquid sorption. This additional freedom of expansion reduces any tendency for the entangled blown fiber web to limit expansion of the web and thereby limit the quantity of water sorbed by the sorbent particles. Crimped transport fibers provide a mechanical release of the web which reduces the constrictive forces on the swelling sorbent particles during liquid sorption. However, the amount of crimp in the fiber cannot be so great as to excessively separate the blown fibers and sorbent particles to the extent that the interstitial movement of fluid though the web is reduced.

The amount of transport fibers included in the sheet product of the invention will depend on the particular use to be made of the product and the amount and type of sorbent particles included in the sheet product. Generally, at least 10 g/m$^2$ of transport fibers per 100 g/m$^2$ of blown fibers will be used to provide sufficient transport and wicking of the sorbed liquid to overcome the blocking effect of swollen sorbent particles and to achieve the desired rapid sorbency. Generally, the amount of transport fiber will not exceed about 100 g/m$^2$ per 100 g/m$^2$ of the blown fibers to maintain the strength and integrity of the blown fiber matrix. Generally, greater amounts of transport fiber may be used when the denier of the fiber is higher. Preferably, the sheet product contains about 20 to 60 g/m$^2$ of transport fibers per 100 g/m$^2$ of the blown fiber. Where high quality, faster sorbency sorbent particles are used, less transport fiber is required to overcome the blocking effect than where low quality sorbent particles are used. In some cases, where the sorbent particles have very rapid sorbency and are present at high loadings in the web, addition of transport fibers of lower water retention values may be unnecessary and even undesirable. Economic considerations, as well as end use requirements, may be used to determine the choice and optimum balance of transport fiber and sorbent particles.

The advantages of the sorbent sheet product of the invention are illustrated in the following examples which are not to be construed as limiting its scope.

In the following Examples, sorbency tests were run using a Demand Sorbency Test which is carried out as follows:

A 4.45 cm (1.75 inch) in diameter test sample of web is placed on a 25–50μ porous plate in a filter funnel. A pressure of 1.0 kPa is applied to the sample by a plunger which is freely movable in the barrel of the funnel. Test fluid at zero dynamic head is conducted from reservoir through a siphon mechanism to the upper surface of the porous plate where the test sample sorbs the test fluid. The amount of test fluid withdrawn from the reservoir by the test sample is then measured to determine the amount of test fluid sorbed by the test sample.

In the Demand Sorbency Tests where synthetic urine is used as the sorbed liquid, the synthetic urine has the following formulation:

| | |
|---|---|
| 0.6% | calcium chloride |
| 0.10% | magnesium sulfate |
| 0.83% | sodium chloride |
| 1.94% | urea |
| 97.07% | deionized water |

The synthetic urine solution has a conductance of 15.7 mΩ.

EXAMPLES 1–7

Sorbent sheet products were prepared from polypropylene microfibers with sorbent particles (Water-Lock J-500 supplied by Grain Processing Corp.) and staple transport fibers of the invention (Examples 1 to 4), comparative staple fibers (Examples 5 and 6), or no staple fiber as indicated in Table 1. The fibers used in these examples are as follows:

rayon—3.3 denier Absorbit rayon staple supplied by American Enka Co.
cotton—2.6–2.7 mike cotton fiber (0.92 denier)
polypropylene—3.0 denier polypropylene staple In each Example, the sorbent sheet contained 110 g/m$^2$ polypropylene microfibers, 150 g/m$^2$ sorbent particles, 0.4 g/m$^2$ anionic surfactant, 1.6 g/m$^2$ glycerol, and staple fiber in the amounts indicated in Table 1. Demand Sorbency Tests were then conducted with synthetic urine on each prepared sheet. The results are shown in Table 1.

TABLE 1

| Example | Staple Fiber Type | Amount of Staple Fiber (g/m$^2$) | Weight of Synthetic urine Sorbed and Retained for Time Shown (1/m$^2$) | | | | |
|---|---|---|---|---|---|---|---|
| | | | 1 min | 2 min | 3 min | 4 min | 5 min |
| 1 | rayon | 20 | 3.0 | 5.0 | 6.3 | 6.8 | 7.0 |
| 2 | rayon | 60 | 3.4 | 5.7 | 7.1 | 7.7 | 7.9 |
| 3 | cotton | 20 | 2.9 | 4.8 | 6.0 | 6.6 | 6.8 |
| 4 | cotton | 60 | 3.2 | 5.3 | 6.8 | 7.7 | 8.2 |
| 5 | polypropylene | 20 | 2.6 | 4.4 | 5.5 | 6.1 | 6.9 |
| 6 | polypropylene | 60 | 2.5 | 4.4 | 5.7 | 6.6 | 7.2 |
| 7 | — | — | 2.5 | 4.2 | 5.2 | 5.7 | 5.9 |

The data of Table 1 shows that the rayon and cotton transport fibers, when used with the J-500 particles at a loading of 150 g/m$^2$, provides the sheet product with more rapid sorbency and increased total sorbency than does the comparative polypropylene fibers. This can be seen when the percent increase in liquid sorbed of the sheet product containing cotton or rayon over the sheet product containing polypropylene is calculated as in Table 2.

TABLE 2

| Staple Fiber Type | Amount of Staple Fiber (g/m$^2$) | Percent Increase in Weight of Synthetic urine Sorbed Over Web Containing Polypropylene Fiber | | | | |
|---|---|---|---|---|---|---|
| | | 1 min | 2 min | 3 min | 4 min | 5 min |
| rayon | 20 | 15.4 | 13.6 | 14.5 | 11.5 | 1.4 |
| cotton | 20 | 11.5 | 9.1 | 9.1 | 8.2 | −1.4 |
| rayon | 60 | 36.0 | 29.5 | 24.6 | 16.7 | 9.7 |
| cotton | 60 | 28.0 | 20.5 | 19.3 | 16.7 | 13.9 |

EXAMPLES 8–14

Sorbent sheet products were prepared as in Examples 1–7, except that the sorbent particles were loaded in the sheet product at 300 g/m$^2$. Demand Sorbency Tests were then conducted with synthetic urine on each prepared sheet. The results are shown in Table 3.

TABLE 3

| Example | Staple Fiber Type | Amount of Staple Fiber (g/m²) | Weight of Synthetic urine Sorbed and Retained for Time Shown (1/m²) | | | | | | |
|---|---|---|---|---|---|---|---|---|---|
| | | | 2 min | 4 min | 6 min | 8 min | 10 min | 12 min | 14 min |
| 8 | rayon | 20 | 3.6 | 6.0 | 7.5 | 8.4 | 8.9 | 9.3 | 9.9 |
| 9 | rayon | 60 | 4.0 | 6.6 | 8.4 | 9.3 | 9.9 | 10.4 | 11.1 |
| 10 | cotton | 20 | 3.0 | 5.1 | 6.4 | 7.2 | 7.8 | 8.2 | 8.9 |
| 11 | cotton | 60 | 3.3 | 5.5 | 7.0 | 7.8 | 8.2 | 8.8 | 9.5 |
| 12 | polypropylene | 20 | 3.2 | 5.3 | 6.8 | 7.5 | 8.1 | 8.5 | 9.1 |
| 13 | polypropylene | 60 | 3.1 | 5.2 | 6.5 | 7.3 | 7.9 | 8.4 | 9.0 |
| 14 | — | — | 3.5 | 5.9 | 7.2 | 7.9 | 8.2 | 8.6 | 9.0 |

The data of Table 3 shows that the rayon transport fiber, at both 20 g/m² and 60 g/m² when used with the J-500 particles at a loading of 300 g/m², provides the sheet product with more rapid sorbency and increased total sorbency. The cotton transport fiber provides improved liquid sorbency at the 60 g/m² level. With the high loading of very rapid sorbency sorbent particles, 20 g/m² of the fine cotton transport fiber was found to be insufficient to provide the desired increase in sorbency. This is seen in Table 4 where the percent increase in weight of water sorbed by the webs containing cotton or rayon over the web containing polypropylene is calculated.

TABLE 4

| Stable Fiber Type | Amount of Staple Fiber (g/m²) | Percent Increase in Weight of Synthetic urine Sorbed Over Web Containing Polypropylene Fiber | | | | | | |
|---|---|---|---|---|---|---|---|---|
| | | 2 min | 4 min | 6 min | 8 min | 10 min | 12 min | 14 min |
| rayon | 20 | 12.5 | 13.2 | 10.3 | 12.0 | 9.9 | 9.4 | 8.8 |
| cotton | 20 | −6.3 | −3.8 | −5.9 | −4.0 | −3.7 | −3.5 | −2.2 |
| rayon | 60 | 29.0 | 26.9 | 29.2 | 27.4 | 25.3 | 23.8 | 23.3 |
| cotton | 60 | 6.5 | 5.8 | 7.7 | 6.8 | 3.8 | 4.8 | 5.6 |

EXAMPLES 15–21

Sorbent sheet products were prepared as in Examples 1–7, except that Water-Lock A-200 sorbent particles, supplied by Grain Processing Corp. were used instead of the J-500 particles. The loading rate of particles was 150 g/m². Demand Sorbency Tests were then conducted with synthetic urine on each prepared sheet. The results are shown in Table 5.

TABLE 5

| Example | Staple Fiber Type | Amount of Staple Fiber (g/m²) | Weight of Synthetic urine Sorbed and Retained for Time Shown (1/m²) | | | | |
|---|---|---|---|---|---|---|---|
| | | | 1 min | 2 min | 3 min | 4 min | 5 min |
| 15 | rayon | 20 | 2.0 | 3.4 | 4.3 | 4.8 | 4.9 |
| 16 | rayon | 60 | 2.1 | 3.4 | 4.1 | 4.4 | 4.5 |
| 17 | cotton | 20 | 1.8 | 3.0 | 3.9 | 4.3 | 4.3 |
| 18 | cotton | 60 | 1.9 | 3.2 | 4.1 | 4.5 | 4.5 |
| 19 | polypropylene | 20 | 1.0 | 1.9 | 2.7 | 3.4 | 3.8 |
| 20 | polypropylene | 60 | 1.2 | 2.3 | 3.4 | 4.1 | 4.5 |
| 21 | — | — | 1.0 | 2.0 | 2.8 | 3.5 | 4.1 |

The data of Table 5 shows that the rayon and cotton transport fibers, when used with the A-200 sorbent particles at a loading of 150 g/m², provide more rapid sorption of the synthetic urine than does polypropylene staple fiber. This can be seen when the percent increase in liquid sorbed of the sheet product containing cotton or rayon over the sheet product containing polypropylene is calculated as in Table 2. The use of rayon or cotton transport fibers also provides a greater increase in sorbency of the sheet product when used with the less sorbent A-200 sorbent particles than when used with the more sorbent J-500 particles.

TABLE 6

| Staple Fiber Type | Amount of Staple Fiber (g/m²) | Percent Increase in Weight Synthetic urine Sorbed Over Web Containing Polypropylene Fiber | | | | |
|---|---|---|---|---|---|---|
| | | 1 min | 2 min | 3 min | 4 min | 5 min |
| rayon | 20 | 100.0 | 78.9 | 59.3 | 41.1 | 28.9 |
| cotton | 20 | 80.0 | 57.9 | 44.4 | 6.5 | 13.2 |
| rayon | 60 | 75.0 | 47.8 | 20.6 | 7.3 | 0 |
| cotton | 60 | 58.3 | 39.1 | 20.6 | 9.8 | 0 |

EXAMPLES 22–28

Sorbent sheet products were prepared as in Examples 15–21, except that the A-200 sorbent particles were loaded at a rate of 300 g/m². Demand Sorbency Tests were conducted with synthetic urine on each prepared sheet. The results are shown in Table 7.

TABLE 7

| Example | Staple Fiber Type | Amount of Staple Fiber (g/m²) | Weight of Synthetic urine Sorbed and Retained for Time Shown (1/m²) | | | | |
|---|---|---|---|---|---|---|---|
| | | | 1 min | 2 min | 3 min | 4 min | 5 min |
| 22 | rayon | 20 | 1.7 | 3.3 | 4.5 | 5.5 | 6.3 |
| 23 | rayon | 60 | 1.7 | 3.4 | 4.7 | 5.8 | 6.4 |
| 24 | cotton | 20 | 1.7 | 3.4 | 4.6 | 5.5 | 5.9 |
| 25 | cotton | 60 | 1.5 | 3.1 | 4.4 | 5.5 | 6.1 |
| 26 | polypropylene | 20 | 0.9 | 1.9 | 2.8 | 3.6 | 4.4 |
| 27 | polypropylene | 60 | 0.8 | 1.6 | 2.3 | 3.0 | 3.7 |
| 28 | — | — | 1.0 | 2.1 | 3.1 | 4.0 | 4.6 |

The data of Table 7 shows that the rayon and cotton transport fibers, when used with the A-200 sorbent particles at a loading of 300 g/m², provide more rapid and higher liquid sorption than do the comparative polypropylene fibers. This can be seen when the percent increase in liquid sorbed of the sheet product containing cotton or rayon over the sheet product containing polypropylene is calculated as in Table 8.

TABLE 8

| Staple Fiber Type | Amount of Staple Fiber (g/m²) | Percent Increase in Weight of Synthetic urine Sorbed Over Web Containing Polypropylene Fiber | | | | |
|---|---|---|---|---|---|---|
| | | 1 min | 2 min | 3 min | 4 min | 5 min |
| rayon | 20 | 88.8 | 73.7 | 60.7 | 52.3 | 43.2 |
| cotton | 20 | 88.8 | 78.9 | 64.3 | 52.3 | 34.1 |
| rayon | 60 | 112.5 | 112.5 | 104.3 | 93.3 | 7.30 |
| cotton | 60 | 87.5 | 93.8 | 91.3 | 83.3 | 64.9 |

EXAMPLES 29–31

A sorbent sheet product of the invention, Example 29, and comparative Examples 30 and 31 were prepared having the constituents shown in Table 6. The initial thickness of each sheet was measured. 5 cm×5 cm samples of each sheet product were prepared and placed in water for 30 seconds. The thickness of each sheet was again measured. Initial and final thicknesses are shown in Table 6.

TABLE 9

| Constituents | Example 29 | Example 30 | Example 31 |
|---|---|---|---|
| Polypropylene microfiber (g/m²) | 100 | 100 | 100 |
| J-500 (g/m²) | 300 | 300 | 13 |
| Rayon *(g/m²) | 60 | — | — |
| Surfactant (g/m²) | 0.4 | 0.4 | 0.4 |
| Glycerol (g/m²) | 1.6 | 1.6 | 0 |
| Initial Thickness (cm) | 0.5 | 0.4 | 0.2 |
| Final Thickness (cm) | 3.5 | 2.0 | 0.7 |

*"Absorbit" rayon fiber supplied by American Enka Co.

What is claimed is:

1. A sorbent sheet product comprising a coherent fibrous web that includes entangled blown fibers and liquid transport fibers intermingled with the blown fibers and an array of solid high sorbency liquid-sorbent polymeric particles uniformly dispersed and physically held within the web, the particles swelling upon sorption of liquid and present in an amount such as to limit rapid permeation of liquid into internal parts of the web, and the transport fibers causing increased and more rapid sorption of liquid by conducting the liquid from external portions of the web to internal portions of the web.

2. A sorbent sheet product of claim 1 wherein the transport fibers are present in an amount of about 10 to 100 g/m² for 100 g/m² of blown fibers.

3. A sorbent sheet product of claim 1 wherein the transport fibers are present in an amount of about 20 to 80 g/m² for 100 g/m² of blown fibers.

4. A sorbent sheet product of claim 1 wherein the transport fibers have a water retention value of at least 20%.

5. A sorbent sheet product of claim 1 wherein the transport fibers are selected rayon, cotton, wool and silk.

6. A sorbent sheet product of claim 1 wherein the transport fibers are rayon.

7. A sorbent sheet product of claim 1 wherein the sorbent particles are present in an amount of at least 20 g/m² for 100 g/m² of blown fibers.

8. A sorbent sheet product of claim 1 wherein the sorbent particles are capable of sorbing 20 or more times their own weight of water.

9. A sorbent sheet product of claim 1 wherein the melt blown fibers comprise microfibers averaging less than about 10 micrometers in diameter.

10. A sorbent sheet product of claim 9 wherein the microfibers are selected from polypropylene, polyethylene, polyethylene terephthalate and polyamide fibers.

11. A sorbent sheet product of claim 8 wherein the sorbent particles are selected from modified starches and acrylic polymers having hydrophilic functionality.

12. A sorbent sheet product of claim 1 wherein the sorbent particles range between 50 and 3000 micrometers in diameter.

13. A sorbent sheet product of claim 1 further comprising surfactant which assists wetting of the web by a liquid to be sorbed are also dispersed within the web fibers.

14. A sorbent sheet product of claim 1 further comprising a binding material.

15. A sorbent sheet product of claim 14 wherein said binding material is glycerol.

16. A sorbent sheet product of claim 8 containing about 35 weight percent blown microfiber, about 50 weight percent sorbent particles and about 15 weight percent transport fibers.

17. A diaper containing the sorbent sheet product of claim 1.

18. An incontinent device containing the sorbent sheet material of claim 1.

19. A filter for separation of water from organic liquids containing the sorbent sheet material of claim 1.

20. A sorbent sheet product of claim 1 wherein said liquid-sorbent polymeric particles are present in an amount of 150 to 300 g/m² for 100 g/m² of the blown fibers.

* * * * *